United States Patent [19]

Lucich et al.

[11] 4,387,438

[45] Jun. 7, 1983

[54] CONTINUOUS TRANSDUCER DRIFT COMPENSATOR

[75] Inventors: George M. Lucich; Charles A. Seitz, both of Amarillo, Tex.

[73] Assignee: The United States of America as represented by the Secretary of the Interior, Washington, D.C.

[21] Appl. No.: 206,247

[22] Filed: Nov. 12, 1980

[51] Int. Cl.³ ............... H04B 15/00; G06G 7/186
[52] U.S. Cl. ............................ 364/574; 328/165; 364/834
[58] Field of Search ............ 364/185, 574, 834; 328/165, 135

[56] References Cited

U.S. PATENT DOCUMENTS

| | | | |
|---|---|---|---|
| 3,231,823 | 7/1962 | Garfield et al. | 328/165 |
| 3,268,824 | 4/1963 | Hinrichs et al. | 328/165 |
| 3,462,240 | 8/1969 | Bosselaar et al. | 328/165 |
| 3,594,557 | 7/1971 | Anderson | 328/135 X |
| 3,605,129 | 9/1971 | Kubanoff | 328/165 |
| 3,757,288 | 9/1973 | Morin | 328/165 X |

Primary Examiner—Felix D. Gruber
Attorney, Agent, or Firm—Thomas Zack; Donald A. Gardiner

[57] ABSTRACT

In a transducer signal processing system wherein the output signal generated by a transducer (14) includes a nearly d.c., relatively large amplitude drift component (12), a higher frequency end point, data component (10) and a high frequency noise (hash) component (11), the drift and hash components are substantially eliminated by supplying the composite transducer output signal to a pair of parallel integrator circuits (28, 30) having different integration time constants. The faster integrator (28) passes the drift and data signal components, while attenuating the hash component, whereas the slower integrator (30) passes the drift component and attenuates the data and hash components. The output of the slower integrator (30) is subtracted from the output of the faster integrator (28) to provide a resultant signal containing essentially only the transducer data component.

3 Claims, 5 Drawing Figures

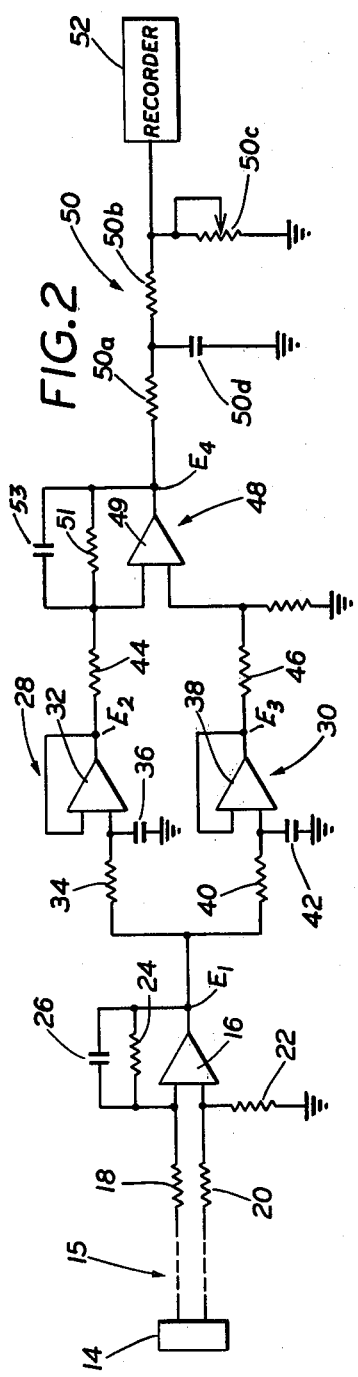
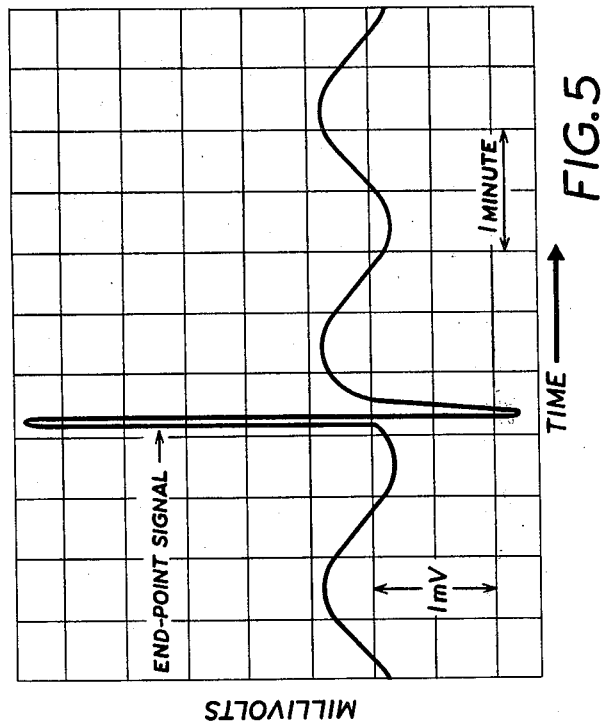
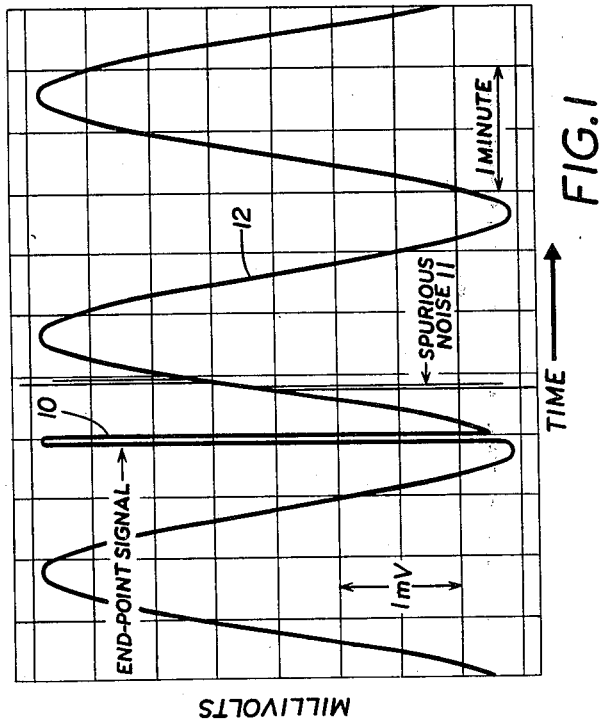

CONTINUOUS TRANSDUCER DRIFT COMPENSATOR

TECHNICAL FIELD

The present invention relates generally to transducer signal processing circuitry and more particularly to circuitry for continuously and automatically compensating a transducer output signal for drift and spurious noise components in an industrial process monitoring system.

BACKGROUND ART

In a standard system for monitoring the end of a helium purification or other process characterized by a sudden release of hydrogen into a helium gas stream, a small amount of air is added to the sample stream from a cryogenic adsorption column and the mixture is passed over a catalyst to form water as a function of hydrogen concentration. Heat generated during formation of water is proportional to the amount of hydrogen in the sample and increases the temperature of the gas exiting the cell. A thermopile containing approximately 20 thermocouples used as a temperature transducer has its "cold end" positioned in the gas stream entering the catalytic cell and its "hot end" positioned in the gas exiting the cell. In the absence of hydrogen, variations in the flow rate of the gas stream as well as variations in ambient temperature cause the output of the thermopile to drift due to its electrothermal asymmetry. The output of the thermopile also contains hash (high frequency noise) caused, among other factors, by current transients developed during switching of electric motors and other heavy electrical equipment. The end of the process is identified by a relatively abrupt output signal generated by the thermopile in response to heat generated following hydrogen release. The hydrogen responsive signal generated by the thermopile is termed herein the transducer end point or data component.

Whereas the period of the drift component is much greater than the period of the end point component of the thermopile output signal, the amplitudes of the two components may be comparable to each other. The hash component typically is at a much lower period with an amplitude sometimes far exceeding the amplitude of the end point component. In practice, a level detector is generally provided to respond to the transducer data or end point signal in the presence of drift and hash to energize an alarm and thereby indicate to a human operator that the end of the process has occurred. In response, the operator manually switches the helium gas stream to a fresh adsorption column and the hydrogen-free sample stream passes through the cell to allow the system to recover. Since the amplitude of the drift signal component may be equal to the amplitude of the data signal component and the amplitude of the hash component may be much greater, however, the data may be swamped so that it is impossible to detect the end point swing of the thermopile.

Whereas the hash component of the composite transducer signal is often eliminated by low pass filtering, the signal processing system must be periodically rebalanced or the drift component alone will exceed the threshold setting of the alarm detector and a false alarm will occur. Intermittent automatic zeroing such as is used in conventional chromatographic systems requires a finite time period for zeroing and thus prevents the system from providing continuous monitoring of the industrial process.

Accordingly, it is an object of the present invention to provide a method of and system for reducing drift and hash in a transducer output signal.

Another object is to provide a method of and system for processing a parameter responsive transducer signal in an end point detection system of a type incorporating a transducer having an output that tends to drift over a period of time.

Another object is to provide a method of and system for drift compensation in an end point detection system of a type using a transducer having an output that drifts very slowly over a period of time and has a drift amplitude that is comparable to the amplitude of a data signal component generated by the transducer.

An additional object of the invention is to provide a method of and system for continuously and automatically zeroing the output of a transducer having a tendency to drift as a function of ambient conditions.

DISCLOSURE OF INVENTION

The output of a thermopile or other transducer that generates or modulates a temperature or other parameter responsive data signal and has a tendency to drift as a function of varying transducer characteristics or varying ambient conditions is applied, following amplification, to first and second parallel integrators having different integration time constants. The shorter time constant (faster) integrator passes the drift and data signal components while attenuating any high frequency noise (hash) superimposed on the output signal. The longer time constant (slower) integrator passes the drift and some data components. The signal developed by the slower integrator (drift and some data) is subtracted from the signal developed by the faster integrator (drift plus data) to obtain a resultant signal containing substantially only a data component.

Still other objects and advantages of the present invention will become readily apparent to those skilled in this art from the following detailed description, wherein we have shown and described only the preferred embodiment of the invention, simply by way of illustration of the best mode contemplated by us of carrying out our invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF DRAWINGS

FIG. 1 is a graph showing a simulated uncompensated transducer output signal including a drift component as well as spurious high frequency noise (hash) superimposed on an end point signal (data) component;

FIG. 2 is a block diagram showing a transducer drift and hash component compensation circuit in accordance with the invention;

FIG. 5 illustrates a recorder record showing the output of the circuit shown in FIG. 2 when the "data signal" has a slew rate of 4 mv/sec for 1 second and returns to zero in 1 second (triangular input) and a "drift" slew rate of 0.066 mv/sec for 60 seconds and return, based upon an input signal $E_1$ as shown in FIG. 1.

Figure 3:
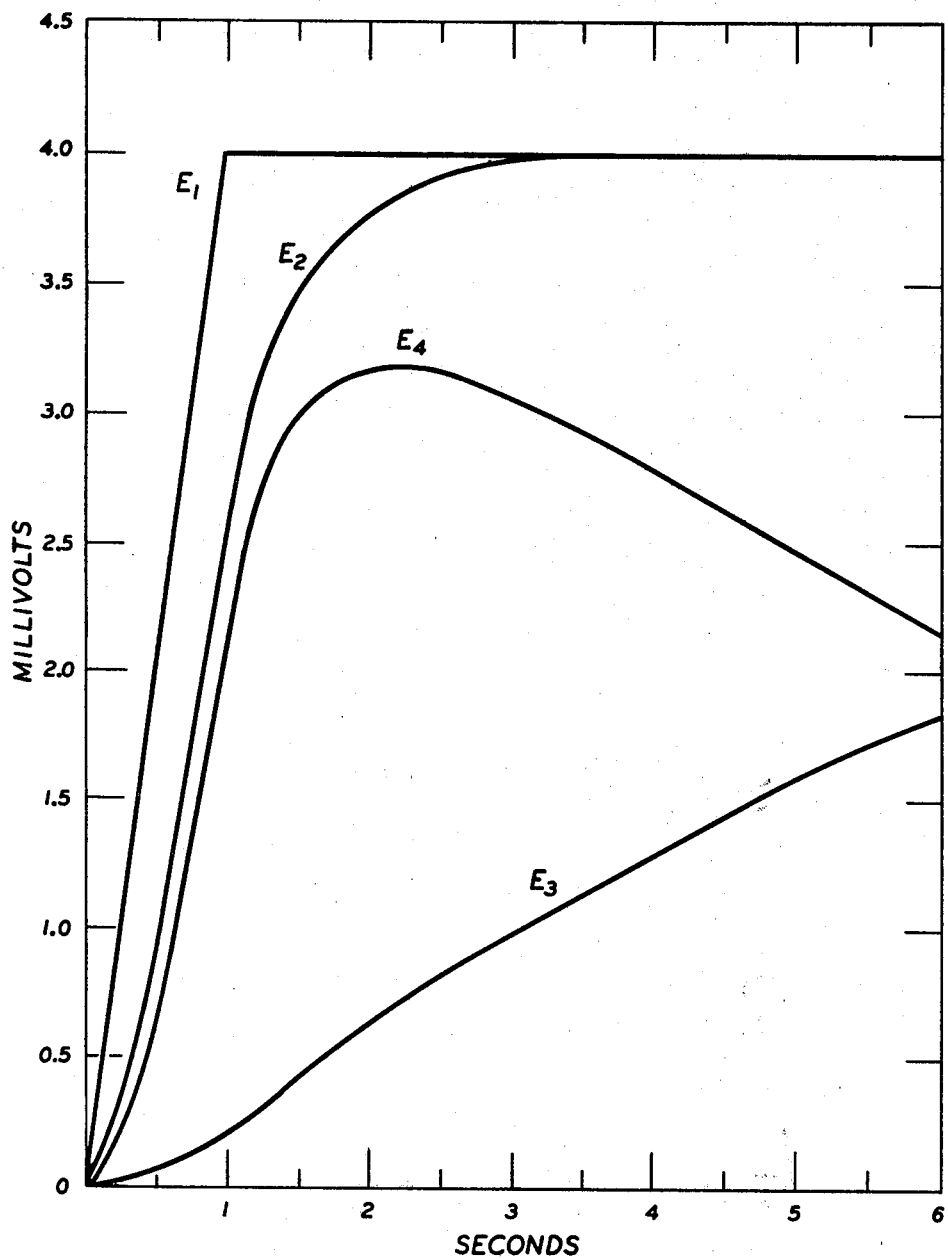
FIG. 3 is a graph showing the output of each amplifier shown in FIG. 2 in response to a ramp and hold input signal.

BEST MODE FOR CARRYING OUT THE INVENTION:

Referring to FIG. 1, a data signal 10 of a type generated by a thermopile, used in monitoring helium purification processes, for example, is superimposed with a slowly changing drift component 12 (low frequency compared to data) as well as with a much higher frequency noise, or hash, component 11. The hash component 11, which has a peak-to-peak amplitude that may be substantially larger than the peak amplitude of end point signal component 10, is typically caused, among other factors, by high current switching waveforms induced on the power lines during operation of motors or other heavy electrical equipment. The drift signal component 12 which has a peak-to-peak magnitude comparable to that of the end point signal 10, is created, among other factors, by slow variation in gas flow and ambient temperature as well as by component aging for the industrial applications.

It is to be understood that the characteristics of the end point signal and drift component signal as well as hash waveforms in practice may differ from the ones shown in FIG. 1. It is to be noted, however, that the slope of the end point signal is generally much greater than the slope of the drift component (on the order of at least one order of magnitude) and that the peak-to-peak amplitudes are comparable to each other (within the same order of magnitude). The frequency of the spurious noise is typically in the RF range with a peak magnitude of several volts.

It is apparent that conventional level detection circuitry, such as a Schmitt trigger, could not be used in this environment for detecting the presence of the end point signal 10 since the end point signal would typically be swamped by the hash component 11 and drift signal component 12, tending to cause the level detector to generate false alarms. In accordance with the invention, the drift and hash signal components are removed from the composite transducer signal by integrating the composite signal at a first integration time constant and also at a second, longer integration time constant and then performing an algebraic subtraction of the two integrator output signals to obtain a resultant signal that contains substantially only the end point component. The shorter time constant integrator develops a signal that is proportional to a sum of the drift and end point signal components with the hash component attenuated. The longer time constant integrator develops a signal that is proportional to the drift component and a small portion of the end point signal (the end point and hash components are attenuated). The algebraic difference between the two integrator signals is thus proportional to only the end point signal.

Referring to FIG. 2, the output of transducer 14 which generates the composite signal shown in FIG. 1 is coupled through lines 15 to the input of a first operational amplifier 16 having a gain of about 1,500 as determined by input resistors 18, 20, 22 and feedback resistor 24. Feedback capacitor 26 attenuates high frequency noise induced on the transducer lines 15. The output of amplifier 16 is coupled to the inputs of both a first integrator 28 and a second integrator 30. Integrator 28 comprises a series resistor 34 and shunt capacitor 36 at the input of an operational amplifier 32 connected in a high impedance, unity gain configuration. Similarly, the second integrator 30 comprises a series resistor 40 and shunt capacitor 42 at the input of an operational amplifier 38 connected in a high input impedance, unity gain configuration. The amplifiers 32, 38 operate as buffers that isolate integration capacitors 36, 42 from other circuitry. The integration time constant of integrator 28 is $R_{34}C_{36}$ whereas that of integrator 30 is $R_{40}C_{42}$. The outputs of the integrators 28 and 30 are coupled through resistors 44 and 46, respectively, to the inputs of a subtractor circuit 48 comprising an operational amplifier 49 connected as a differential amplifier together with feedback resistor 51 and capacitor 53. The output of subtracter 48, which is proportional to the algebraic difference between the two signals generated, respectively, by integrators 28 and 30, is coupled through a variable attenuator 50 to a recorder 52. Attenuator 50, which provides ranging for the recorder 52, comprises series resistors 50a, 50b and shunt potentiometers 50c. A shunt capacitor 50d attenuates spurious signals impressed on the output of amplifier 49 by the recorder 52 and other noise sources.

The output E of integrator 28 or integrator 30 in response to a ramp function input is given by the following equation:

$$E=(KRC-B+E_I)e^{-t/RC}-KRC+B+Kt \qquad (1)$$

where
E = output voltage of amplifier 32 or amplifier 38,
$E_I$ = initial output voltage of amplifier 32 or amplifier 38,
B = initial output voltage of amplifier 16,
t = time in second after application of input signal to amplifier 16,
RC = $R_{34}C_{36}$ (short time constant for amplifier 32) or $R_{40}C_{42}$ (long time constant for amplifier 38), and
K = proportionality constant in millivolts per second for output of amplifier 16.

Finally, the output $E_4$ of subtractor 48 is given by the following equation:

$$E_4=E_2-E_3 \qquad (2)$$

where
$E_2$ = the output voltage of amplifier 32, and
$E_3$ = the output voltage of amplifier 38.

The responses of amplifier 16, integrators 28, 30 and subtracter 48 to a ramp input signal are shown respectively by waveforms $E_1$, $E_2$, $E_3$ and $E_4$ in FIG. 3. Similarly, the corresponding responses to a triangular input are shown respectively by waveforms $E_1'$, $E_2'$, $E_3'$ and $E_4'$ in FIG. 4. In each case, the output $E_3$, $E_3'$ of the longer time constant integrator 30 lags behind the output $E_2$, $E_2'$ of integrator 28 and the output of subtracter 48 is equal to the algebraic difference between the outputs of integrators 28 and 30.

Figure 4:
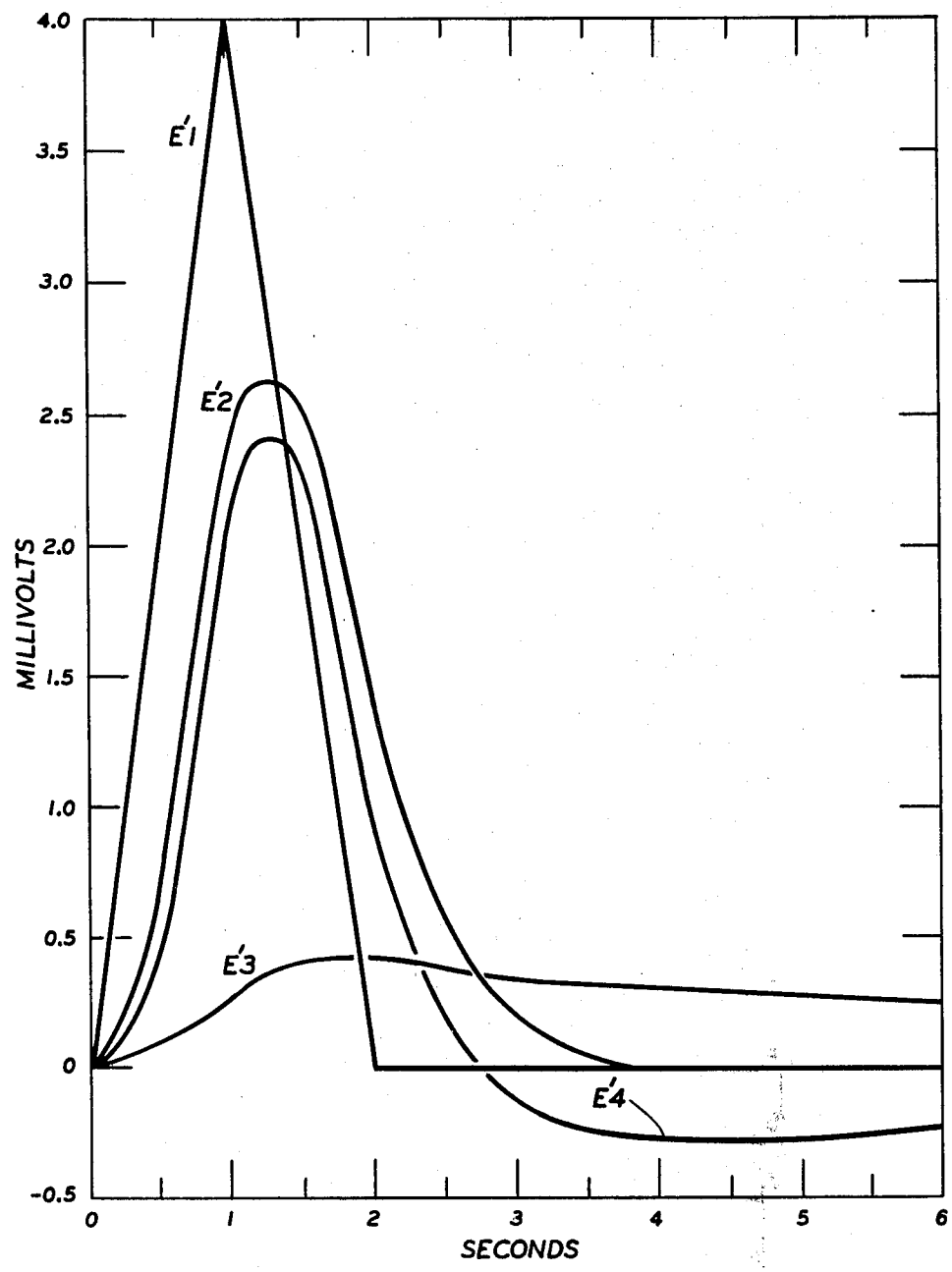
FIG. 4 is a graph showing the output of each of the amplifiers in response to a triangular input waveform simulating a data signal with no drift present.

The triangular input waveform of FIG. 4 approximates the end point signal 10 generated by transducer 14 whereas the ramp input waveform having a constant magnitude at steady state approximates the drift component 12. By inspection of FIGS. 3 and 4, it is clear that, whereas the shorter time constant integrator 28 must be slow enough to effectively attenuate high frequency hash, the integrator undesirably attenuates the end point signal; the shorter integrator time constant should thus be as fast as possible to minimize end point signal attenuation. The longer time constant integrator 30 should be slow enough to effectively attenuate all frequency components above the drift component frequency but should not be so slow as to attenuate the drift component.

We have measured the following parameters in a typical helium purification system of a type described supra:

| end point signal rise rate | ~1mV/sec (at output of amplifier 16) |
|---|---|
| duration of end point signal variable | |
| drift signal rise rate | ~1mV/20 min. (worst case) |
| noise signal | 1mV @ 0-10Hz. |

We have determined that optimum processing of the transducer signal whereby drift and hash are substantially eliminated with minimum attenuation of the end point signal occurs under the following set of conditions:

$$T_{fast} < m/V_s \quad (3)$$

$$T_{slow} > n\, T_F \quad (4)$$

where $V_s$ is the slew rate of data signal 10 given in mV/sec,
m = 3 mV and
n = 10.

Based on the above system parameters and on equations (3) and (4), we have obtained the following integration time constant values:

$T_{fast} = 0.5$ sec.
$T_{slow} = 9$ sec. for the laboratory test shown in FIG. 5.

The resultant signal applied to recorder 52 using the above described circuit and integration time constant values has been verified experimentally to have substantially reduced drift and hash as shown in FIG. 5 for the laboratory controlled input (compare with FIG. 1). Even any drift developed within amplifier 16 is compensated together with transducer generated drift in integrators 28, 30 and subtractor 48. Of particular importance, zeroing of the output signal (drift compensation) is provided continuously; there is no need to periodically interrupt monitoring to initiate a zeroing cycle.

In this disclosure, there is shown and described only the preferred embodiment of the invention, but, as aforementioned, it is to be understood that the invention is capable of use in various other combinations and environments and is capable of changes or modifications within the scope of the inventive concept as expressed herein. It is apparent, for example, that the compensation circuit configuration of this invention is not limited to the particular embodiment described herein and that the circuit can be used in applications other than thermopile drift compensation.

What is claimed is:

1. A circuit for reducing the d.c. outputted drift signal component from a transducer generated signal wherein the transducer signal includes the d.c. drift component to be reduced, a data component, and a high frequency noise component, said circuit comprising:

first and second parallel integrator circuit means which receive and are responsive to said transducer signal;

said first integrator circuit means having a first time constant set to pass the d.c. drift and data components of the received transducer signal while attenuating its received noise component;

said second integrator circuit means having a second time constant set to be longer than the first time constant, said second integrator circuit means passes the said received d.c. drift and a smaller portion of the data component than that passed by the first integrator circuit means, said two integrator circuit means generating, respectively, first and second output signals; and circuit means for receiving said first and second output signals from the integrators and for subtracting said second output signal from said first output signal, the output signal from said subtracting means being a data component signal whose drift and noise component are continuously and automatically suppressed therein.

2. The circuit of claim 1, including display means coupled to said subtracting means for displaying said output signal therefrom.

3. The circuit of claim 2, including attenuator means coupled to said subtracting means for ranging said drift suppressed output signal for display on said display means.

* * * * *